(12) United States Patent
Perryman et al.

(10) Patent No.: US 10,994,149 B2
(45) Date of Patent: May 4, 2021

(54) WIRELESS IMPLANTABLE POWER RECEIVER SYSTEM AND METHODS

(71) Applicant: Stimwave Technologies Incorporated, Miami Beach, FL (US)

(72) Inventors: Laura Tyler Perryman, Scottsdale, AZ (US); Chad Andresen, Chandler, AZ (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 5 days.

(21) Appl. No.: 14/214,241

(22) Filed: Mar. 14, 2014

(65) Prior Publication Data

US 2014/0275847 A1  Sep. 18, 2014

Related U.S. Application Data

(60) Provisional application No. 61/786,069, filed on Mar. 14, 2013.

(51) Int. Cl.
*A61N 1/378* (2006.01)
*A61N 1/39* (2006.01)
(Continued)

(52) U.S. Cl.
CPC .......... *A61N 1/3787* (2013.01); *A61B 5/0205* (2013.01); *A61B 5/0402* (2013.01);
(Continued)

(58) Field of Classification Search
CPC .............. A61N 1/3787; A61N 1/36125; A61N 1/37223; A61N 1/37229; A61N 1/37205;
(Continued)

(56) References Cited

U.S. PATENT DOCUMENTS 6,107,699 A * 8/2000 Swanson ............ A61B 18/1492
  307/112
7,260,436 B2 * 8/2007 Kilgore .............. A61N 1/36003
  607/2

(Continued)

FOREIGN PATENT DOCUMENTS

CN 101081324 12/2007
CN 102429807 5/2012
(Continued)

OTHER PUBLICATIONS

International Search Report in International Application No. PCT/US2014/029187, dated Aug. 12, 2014, 2 pages.
(Continued)

*Primary Examiner* — Niketa I Patel
*Assistant Examiner* — Nathan A Baldwin
(74) *Attorney, Agent, or Firm* — Fish & Richardson P.C.

(57) ABSTRACT

A method and system is presented for an implantable wireless power receiver for use with a medical stimulation or monitoring device. The receiver receives transmitted energy through one or more non-inductive antenna(s), utilizes microelectronics to perform rectification of the received signal for generation of a DC power supply to power an implantable device, and may also utilize microelectronics to provide parameter settings to the device, or stimulating or other waveforms to a tissue.

42 Claims, 10 Drawing Sheets

(51) Int. Cl.
*A61N 1/362* (2006.01)
*A61N 1/36* (2006.01)
*A61B 5/0476* (2006.01)
*A61B 5/0402* (2006.01)
*A61B 5/0205* (2006.01)
*A61B 5/00* (2006.01)
*A61B 5/145* (2006.01)
*A61B 5/053* (2021.01)
*A61N 1/05* (2006.01)
*A61N 1/04* (2006.01)
*A61M 5/142* (2006.01)
*A61M 5/172* (2006.01)

(52) U.S. Cl.
CPC .......... *A61B 5/0476* (2013.01); *A61B 5/4836* (2013.01); *A61B 5/686* (2013.01); *A61N 1/362* (2013.01); *A61N 1/36038* (2017.08); *A61N 1/36125* (2013.01); *A61N 1/3975* (2013.01); *A61B 5/053* (2013.01); *A61B 5/14503* (2013.01); *A61B 5/14532* (2013.01); *A61B 2560/0219* (2013.01); *A61M 5/14276* (2013.01); *A61M 2005/1726* (2013.01); *A61N 1/0472* (2013.01); *A61N 1/056* (2013.01); *A61N 1/0529* (2013.01)

(58) Field of Classification Search
CPC ................. A61N 1/3975; A61B 5/686; A61B 2560/0219
See application file for complete search history.

(56) References Cited

U.S. PATENT DOCUMENTS

| | | | | |
|---|---|---|---|---|
| 7,519,421 | B2* | 4/2009 | Denker | A61N 1/36114 607/122 |
| 7,813,809 | B2 | 10/2010 | Strother | |
| 2005/0090756 | A1* | 4/2005 | Wolf | A61N 1/08 600/546 |
| 2006/0161225 | A1* | 7/2006 | Sormann | A61B 5/0031 607/61 |
| 2007/0282383 | A1 | 12/2007 | Koyama | |
| 2011/0124310 | A1 | 5/2011 | Theilmann | |
| 2011/0241959 | A1* | 10/2011 | Georgescu | H01Q 1/38 343/793 |
| 2011/0248903 | A1* | 10/2011 | Blick | H01Q 1/248 343/904 |
| 2012/0032200 | A1 | 2/2012 | Kwon | |
| 2012/0197099 | A1 | 8/2012 | Goodnow | |
| 2012/0197342 | A1* | 8/2012 | Towe | A61N 1/06 607/45 |
| 2012/0203129 | A1* | 8/2012 | Rennaker, II | A61B 5/04001 600/544 |
| 2012/0283800 | A1 | 11/2012 | Perryman et al. | |
| 2012/0330384 | A1 | 12/2012 | Perryman et al. | |
| 2013/0018439 | A1 | 1/2013 | Chow et al. | |
| 2013/0018440 | A1* | 1/2013 | Chow | A61N 1/3787 607/61 |
| 2013/0123882 | A1 | 5/2013 | Towe | |
| 2015/0100110 | A1* | 4/2015 | Towe | A61N 1/36125 607/61 |
| 2015/0297900 | A1 | 10/2015 | Perryman | |

FOREIGN PATENT DOCUMENTS

| | | |
|---|---|---|
| CN | 102600011 | 7/2012 |
| JP | 2002524124 | 8/2002 |
| JP | 2008006275 | 1/2008 |
| JP | 2014514070 | 6/2014 |
| JP | 2014513562 | 8/2014 |
| JP | 2014524279 | 9/2014 |
| WO | WO-2012/103519 A2 | 8/2012 |
| WO | WO-2012/138782 | 10/2012 |
| WO | WO 2012139063 | 10/2012 |
| WO | WO-2013/019757 | 2/2013 |
| WO | WO-2013/025632 | 2/2013 |
| WO | WO-2013/040549 | 3/2013 |
| WO | WO 2014/089299 A2 | 6/2014 |

OTHER PUBLICATIONS

Written Opinion of the International Searching Authority in International Application No. PCT/US2014/029187, dated Aug. 12, 2014, 8 pages.
International Preliminary Report on Patentability in International Application No. PCT/US2014/029187, dated Sep. 15, 2015, 9 pages.
Chinese Office Action in Chinese Application No. 201480023095.7, dated Nov. 30, 2016, 31 pages.
Chinese Office Action in Application No. 201480023095.7, dated Aug. 11, 2017, 77 pages (with English translation).
Australian Office Action in Application No. 2014236294, dated Sep. 1, 2017, 4 pages.
Mexican Office Action in Application No. MX/a/2015/012255, dated Jun. 26, 2017, 3 pages.
Japanese Office Action in Japanese Application No. 2016-503005, dated May 2, 2018, 14 pages.
Australian Notice of Allowance in Australian Application No. 2014236294, dated Jun. 27, 2018, 3 pages.
Israel Office Action in Application No. 241267, dated Mar. 13, 2019, 5 pages.
EP Search Report in European Appln. No. 14771023.0, dated Jan. 9, 2016, 7 pages.
Japanese Notice of Allowance in Japanese Appln. No. 2016-503005, dated Dec. 3, 2019, 9 pages (with English Translation).

* cited by examiner

WIRELESS IMPLANTABLE POWER RECEIVER SYSTEM AND METHODS

CROSS-REFERENCE TO RELATED APPLICATIONS

This application claims the benefit of and priority to U.S. Provisional Patent Application No. 61/786,069, which was filed on Mar. 14, 2013. The foregoing U.S. provisional application is incorporated by reference herein in its entirety.

BACKGROUND

Various devices are used within the body for a multitude of therapeutic applications. For instance, devices may be used to deliver stimulatory signals, record vital signs, perform pacing or defibrillation operations, record action potential activity from targeted tissue, control drug release from time-release capsules or drug pump units, or interface with the auditory system to assist with hearing. Typically, a subcutaneous battery operated implantable pulse generator (IPG) or other charge storage mechanism is used to provide power to a device.

However, devices which utilize a battery or other charge storage component are no longer functional once the battery or charge storage component can no longer retain charge. Consequently, for an implanted device, a patient would need to undergo a subsequent surgical procedure to obtain a replacement device. In addition, rechargeable IPGs cannot typically administer therapy while the unit is being recharged.

By utilizing the technology incorporated within the implantable wireless power receiver, which does not rely upon a battery or other charge storage device for operation, the life of an implanted device is no longer limited by the life of the battery or the ability to store charge. Further, such technology facilitates a smaller form factor, which results in a less invasive surgical procedure for placement of the device, and helps to reduce scarring from a reduction in the amount of bodily tissue in contact with the implanted device.

SUMMARY

One embodiment of the present disclosure relates to a wireless implantable power receiver for use with a medical stimulation or monitoring device. The wireless implantable power receiver includes one or more non-inductive antennas and electronic circuitry. The one or more non-inductive antennas are configured to receive radiated energy, and the electronic circuitry is configured to convert the radiated energy received by the one or more non-inductive antennas to a DC power supply to provide power to a medical stimulation or monitoring device. The DC power supply operatively powers the medical stimulation or monitoring device such that the medical stimulation or monitoring device does not require the use of battery power or wired power from another power source. In one embodiment, the electronic circuitry configured to generate a DC power supply further includes a rectification circuitry and a smoothing circuitry. The rectification circuitry and the smoothing circuitry may be passive and further include one or more diodes. The smoothing circuitry may further include one or more resistors and one or more capacitors. The electronic circuitry may provide up to 10 Volts DC power to the medical stimulation or monitoring device. The wireless implantable power receiver may be physically integrated within an enclosure of the medical stimulation or monitoring device. The electronic circuitry may deliver power to a plurality of sensors of the medical stimulation or monitoring device.

Another embodiment of the present disclosure relates to a wireless implantable power receiver for a medical stimulation or monitoring device. The receiver includes one or more non-inductive antennas configured to receive radiated energy. The receiver further includes electronic circuitry configured to convert the radiated energy received by the one or more non-inductive antennas. The radiated energy may be converted into one of a DC power supply to provide power to the medical stimulation or monitoring device; a signal to provide parameter settings to the medical stimulation and monitoring device; a waveform to provide stimulatory signals to a tissue; or any combination thereof. The conversion of energy received by the one or more non-inductive antennas may provide the primary source of power to the medical stimulation or monitoring device. The receiver may be enclosed in a housing shared by the medical stimulation and monitoring device. An outside diameter of the receiver may be less than an inside diameter of a 14 gauge cannula or syringe. The receiver may include a conditioning circuitry configured to condition the received energy. At least one of the non-inductive antennas may include conductive trace on one of the circuits. At least one of the non-inductive antennas may be fabricated as a conductive wire connected to one of the circuits. The one or more non-inductive antennas may have a length ranging from about 100 microns to about 10 cm. The one or more non-inductive antennas may have a thickness ranging from about 20 microns to about 3 mm. The one or more non-inductive antennas receive frequencies from about 300 MHz to about 8 GHz. The parameter settings distributed to the device may include frequency, amplitude and duration parameters. The receiver may further include electronic circuitry to transmit signals recorded by the device to a remote system for storage or processing. The remote system may process signals transmitted by the receiver, to produce parameter signals, tissue stimulation signals, or both, which are transmitted to the implantable power receiver for distribution to elements of the device. A system including a plurality of wireless implantable power receivers, in which each wireless implantable power receiver is arranged in series, with respect to one another, may produce a power supply that is greater than 10 Volts DC power.

Another embodiment of the present disclosure relates to a system for use with a medical device. The system includes one or more medical stimulation or monitoring devices. The system further includes one or more non-inductive antennas configured to receive radiated energy. The system further includes electronic circuitry configured to convert the radiated energy received by the one or more non-inductive antennas into: (i) a DC power supply to provide power to the one or more medical stimulation or monitoring devices; (ii) a signal to provide parameter settings to the one or more medical stimulation or monitoring devices; (iii) a waveform to provide stimulatory signals to a tissue via a conductor implanted near the tissue; or (iv) any combination thereof. The one or more medical stimulation or monitoring devices is selected from the group consisting of: (a) a glucose monitor; (b) a cardiac device for monitoring, pacemaking or defibrillation; (c) one or more internal sensors for measuring vital signs; (d) one or more external sensors, such as EEG or ECG sensors, for measuring electrical activity; (e) microwires which measure action potential activity; (f) a time-release capsule or a drug-release device; (g) a cochlear lead; and (h) a deep brain stimulation device.

Another embodiment relates to a medical device system. The medical device system includes a medical stimulation or monitoring device and a wireless implantable power receiver. The wireless implantable power receiver includes one or more non-inductive antennas and electronic circuitry. The one or more non-inductive antennas are configured to receive radiated energy. The electronic circuitry is configured to convert the radiated energy received by the one or more non-inductive antennas to a DC power supply to provide power to the medical stimulation or monitoring device. The medical stimulation or monitoring device may exclude one or more electrodes configured to apply one or more electrical pulses to a neural tissue associated with the spinal column. The electronic circuitry configured to generate a DC power supply may further include a rectification circuitry and a smoothing circuitry. The rectification circuitry and the smoothing circuitry may be passive. The rectification circuitry may further include one or more diodes. The smoothing circuitry may further include one or more resistors and one or more capacitors. The wireless implantable power receiver may be configured to provide up to 10 Volts DC power. The wireless implantable power receiver may be physically integrated within the body of the medical stimulation or monitoring device. The wireless implantable power receiver may be tethered by one or more wires to the medical stimulation or monitoring device. The wireless implantable power receiver may provide power to a plurality of sensors within the medical stimulation or monitoring device.

Another embodiment of the present disclosure relates to a method of delivering electrical signals to power to a medical stimulation or monitoring device. The method includes enclosing the implantable wireless power receiver within the medical stimulation or monitoring device, implanting the receiver and the medical stimulation or monitoring device into tissue, receiving and converting radiated energy into a DC power supply for distribution to the medical stimulation or monitoring device, and operating the medical stimulation or monitoring device without receiving power from a source other than the DC power supply. The receiving step may be completed using non-inductive antennas. The power may provided to the medical stimulation or monitoring device without receiving power from a battery for the medical stimulation or monitoring device and without receiving power from a battery of the receiver. The method may further include using radiated energy received by one or more non-inductive antennas and converting the radiated energy using electronic circuitry into a parameter input for distribution to the device, and delivering the parameter input to the device. The parameter may have at least three different possible values. The method may further include receiving radiated energy from one or more non-inductive antennas and converting the radiated energy using electronic circuitry into an electrical waveform suitable for tissue simulation, and delivering the waveform to the device for distribution into the tissue, and stimulating the tissue.

DETAILED DESCRIPTION

Figure 1:
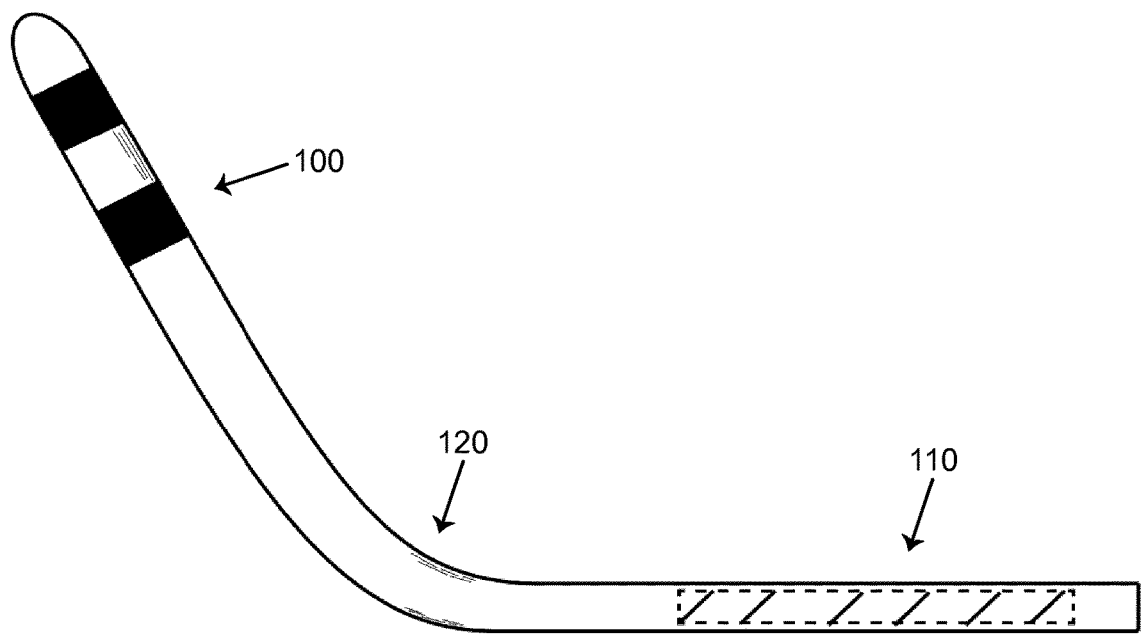
FIG. 1 illustrates an implantable power receiver system powering stimulation or recording electrodes, according to an exemplary embodiment.

The systems, methods and apparatus described in this application relate to transmitting and modulating energy and signals into and through a wireless power receiver that is fully contained within the body of an implantable device. The wireless implantable power receiver can include one or more non-inductive antennas for receiving wireless or radiated energy from a remote source. The wireless implantable power receiver can also include one or more electronic circuits for harnessing the wireless energy and transforming such energy into a power source that is routed to the other elements of the device that provide therapeutic function or monitoring. The wireless implantable power receiver (herein referred to as "receiver") may be used to power medical devices (e.g., implantable medical stimulation and/or monitoring devices, devices which include neurostimulation functions, pacing, identification, telemetry, sensing or other body monitoring functions, etc.).

Embodiments of the present invention include a system for providing power in a form factor that can be fully contained within a device, along with parameter information embedding on an analog waveform(s) when applicable. Such a system may further be easily placed within tissue or reside within close contact to the targeted tissue. Additionally, such a system can reside at a location in which electrical signals from electrical radiative coupling is adequately received by the system at various tissue depths. Such a system is preferably wireless, and does not use cables or inductive coupling to power the implantable power receiver. Such a system may not use, contain, or rely on wired connectors or connector pads (e.g., a providing a physical electrical connection, providing close inductive coupling, etc.).

One embodiment relates to a wireless implantable power receiver including one or more non-inductive antennas and electronic circuitry. The one or more non-inductive antennas are configured to receive radiated energy. The electronic circuitry is configured to convert the radiated energy received by the one or more non-inductive antennas to a DC power supply to provide power to the device. The medical device can exclude a connector for receiving a wire or for receiving power from a source other than the DC power supply. In some embodiments, the power supplied by the DC power supply based on the radiated energy received is sufficient to power the medical device without supplemental power. In an exemplary embodiment, the medical device does not include a long term battery for energy storage but rather uses the "live" receipt of energy at the antenna to power the circuitry and to power the medical device's primary function.

In some embodiments, the wireless implantable power receiver is not connected indirectly via a length of thin wire to a lead containing electrodes for stimulation of tissues associated with the spinal column, but, instead, is fully integrated into an overall system in which the wireless implantable power receiver provides power directly to a component or device, which is itself implantable. A wireless implantable power receiver can attach directly to a component or device (e.g., medical device) that is in need of a DC power supply. In other embodiments, the receiver may provide power to a plurality of sensors distributed throughout a device. In still other embodiments, a plurality of receivers are arranged in series, with respect to one another, to produce a power supply that is greater than 10 Volts DC power.

Another embodiment relates to a wireless implantable power receiver including one or more non-inductive antennas configured to receive radiated energy. The receiver can also include electronic circuitry configured to convert the radiated energy received by the one or more non-inductive antennas into: (i) a DC power supply to provide power to one or more devices; (ii) a signal to provide parameter settings to the device; (iii) a waveform to provide stimulatory signals to a tissue; or (iv) any combination thereof. The receiver can exclude a wired connector for receiving the power.

A wireless implantable power receiver includes one or more non-inductive antennas and electronic circuitry, in which the one or more non-inductive antennas are configured to receive radiated energy, and the electronic circuitry is configured to convert the radiated energy received by the one or more non-inductive antennas to a DC power supply to provide power to one or more devices, wherein the device excludes one or more electrodes configured to apply one or more electrical pulses to a neural tissue associated with the spinal column.

Accordingly, the present invention provides a wireless implantable power receiver system. The system includes an enclosure, the enclosure housing, and one or more non-inductive antenna(s) configured to receive, from a remote antenna through electrical radiative coupling, an input signal containing electrical energy. The system further includes one or more circuits electrically connected to the one or more non-inductive antenna(s), configured to convert the electrical energy contained in an input signal to a DC constant power source. The enclosure, in certain embodiments, is shaped and arranged for delivery into a subject's body through an introducer or needle. In another embodiment, a relay antenna which is physically separate from the remote antenna is used to transmit energy to the implantable power receiver. In still another embodiment, the implantable power receiver may additionally deliver parameters to a device, or waveforms to tissue, or both. Distinctively, the invention disclosed here does not connect to a separate device as detailed in provisional U.S. patent application, 61/733,867, which utilizes a connector to provide power only to an attached device. Embodiments of the present invention can provide, not only power, but also parameter sets and instructions to circuitry (e.g., circuitry of the medical stimulation or monitoring device). The receiver circuitry and the medical device circuitry can be contained within the same housing or enclosure, according to an exemplary embodiment.

Further descriptions of exemplary wireless systems for providing neural stimulation to a patient can be found in co-pending published PCT applications PCT/US2012/23029 filed Jan. 27, 2012, PCT/US2012/32200 filed Apr. 4, 2012, PCT/US2012/48903, filed Jul. 30, 2012, PCT/US2012/50633, filed Aug. 13, 2012 and PCT/US2012/55746, filed Sep. 17, 2012, the complete disclosures of which are hereby incorporated by reference in their entirety for all purposes.

In still another embodiment of the invention, one or more circuits of the implantable power receiver, preferably, include only passive components. In another embodiment, the rectification circuitry and the smoothing circuitry are passive. In yet other embodiments, the one or more circuits are active (e.g., an active integrated circuit, field programmable gate array, or another active controller that can be powered for a brief period of time and conduct its task using power provided by the receiver circuitry).

In yet another embodiment of the invention, the implantable power receiver, preferably, does not include connectors (e.g., wired connectors) or connector pads (e.g., inductive pads), differentiating the device from the prior art. In still further embodiments, the implantable power receiver does not include a built-in long term storage battery. In still further embodiments, neither the receiver nor the medical device powered by the receiver contains a long term storage battery. In still further embodiments, the receiver and/or the medical device contain a battery used for backup purposes or other secondary purposes while the primary power is provided via the receiver circuitry.

Internal circuitry of the implanted wireless receiver system functions to provide power to the device electronics within the enclosure and to convert the incoming wireless energy signal (e.g. radiated energy) into an electrical waveform, or to distribute to portions of the device.

In one embodiment, the internal circuitry may include one or a plurality of diodes. It should be noted that diodes function to rectify the wireless signal, such as a sinusoidal signal, received by the non-inductive antenna(s). The diodes have a low threshold voltage to maximize the energy used for creating waveforms and power. Additionally, the circuitry may include a charge balancing microelectronic component to reduce or prevent corrosion as well as a current limiter.

In certain embodiments, the circuitry may include one or more non-inductive antennas, a rectifier, a charge balancer, a current limiter, a controller, and a device interface. In brief, the rectifier functions to rectify the signal received by the one or more non-inductive antennas. The rectified signal may be fed to the controller for receiving encoded instructions from a RF pulse generator module. The rectified signal may also be fed to a charge balance component that is configured to create one or more electrical pulses such that the one or more electrical pulses result in a substantially zero net charge (that is, the pulses are charge balanced). The charge balanced pulses are passed through the current limiter to the device interface. An example of this type of circuitry is described in additional detail in PCT/US2012/023029, which is fully incorporated by reference. The reader is referred to this published international application for additional details. Additionally, the reader is referred to published U.S. Application 2012/0330384, which is also fully incorporated by reference.

In other embodiments of the presently claimed invention, the implantable power receiver is not connected to electrodes configured to apply one or more electrical pulses to a neural tissue associated with the spinal column.

In still another embodiment, the wireless implantable power receiver does not include a connector or one or more connector pads. The reader is referred to published international application PCT/US2012/032200, which is also incorporated by reference, for additional details.

A telemetry signal may be transmitted to the implantable power receiver to deliver parameters to the device. The telemetry signal may be sent by modulation of a carrier signal. The telemetry signal does not interfere with the received input signal which is transformed into a DC power supply to power the device. In one embodiment, the telemetry signal and powering signal are combined into one signal; separate electronic subsystems harness the power contained in the signal and extract the data content of the signal.

An RF pulse generator system may be located externally to the body or implanted within tissue remotely from the implanted power receiver. The RF pulse generator system can, in certain embodiments, store parameters that are transmitted to an implanted power receiver via a remote antenna.

In preferred embodiments, the implantable power receiver is integrated or embedded within the device to which it provides power. In other embodiments, the power receiver may be tethered to a device through a conductive wire. The receiver may be tethered by one or more wires to a separate device, not by a connector. In still other embodiments, the device is physically integrated within a medical device enclosure.

The implanted power receiver system can include an enclosure that houses one or more non-inductive antennas (for example, dipole or patch antennas), include internal circuitry including microelectronics for electrical energy rectification, and be connected to an implanted device or device in close contact with human tissue.

In certain embodiments, at least one of the antennas can be constructed as a conductive trace feature contained on one of the circuits. In another embodiment, at least one of the antennas can be fabricated as a conductive wire connected to one of the circuits.

In various embodiments, the implantable power receiver is powered wirelessly (and therefore does not require a wired connection) and contains the circuitry necessary to receive pulse instructions and waveforms or other signals from a source external to the body. For example, various embodiments employ non-inductive, for example, dipole or other antenna configuration(s), to receive RF power through electrical radiative coupling.

Furthermore, the electrical radiative coupling mechanism (for example, a dipole antenna) can be utilized to improve the form factor of a wireless implantable power receiver and allow for miniature diameters, as small as 30 microns. Other implementations can have diameters of less than 1.3 mm, or as small as 300 microns.

Electrical radiative coupling also allows for the transmission and reception of energy at greater depths with less degradation in efficiency than inductive coil techniques. This can provide an advantage over devices that employ inductive coupling since the efficiency of such implants is highly dependent on the distance separating the external transmitter coil and the implanted receiver coil.

Various energy-coupling structures are included in this invention. Some embodiments have only one non-inductive antenna; other embodiments have one or more non-inductive antennas, or a plurality of non-inductive antennas of any given width. For example, without limitation, some embodiments have between three and ten non-inductive antennas, while other embodiments can have more than ten non-inductive antennas. Still other embodiments can have more than twenty non-inductive antennas.

In another embodiment, the non-inductive antenna(s) and the microelectronics can be placed singularly or in a multitude.

The antenna is a non-inductive antenna and is configured to receive, through electrical radiative coupling, an input signal containing electrical energy. In certain embodiments, the source of radiative energy is physically separate from the implantable power receiver. That is, the source is remote from the implantable power receiver, and the source itself transmits the energy, for example, electromagnetic radiation, wirelessly. Of course, the source of radiated energy is positioned at some proximity (but not physically in contact with or electrically connected by wires) to the implantable power receiver so that the one or more non-inductive antennas can receive the radiated energy.

Embodiments of this disclosure use electrical coupling and high frequencies to penetrate tissue mediums without direct contact of the transmission antenna to the body, as described and incorporated by reference in PCT Application PCT/US2012/023029.

In various embodiments, the implantable power receiver may be used to receive radiated energy from a remote source and provide power, parameters and waveforms to a device without using cables or inductive coupling to power the implantable power receiver.

The antenna can be, for example, a dipole antenna. Some embodiments may have only one dipole antenna, other embodiments may have multiple antennas of any given length. For example, without limitation, some embodiments may have between two and ten dipole antennas, while other embodiments can have more than ten dipole antennas or more than twenty dipole antennas.

In other embodiments, the implantable power receiver system may include up to ten non-inductive antennas within the enclosure, each independently having a length ranging from one-quarter of a centimeter to twelve centimeters.

In some other embodiments, a dipole antenna or non-inductive antenna can range from about 100 microns to about 10 cm in length. In other embodiments, a non-inductive antenna can range from 0.25 cm to 12 cm in length.

In other embodiments, a non-inductive antenna can consist of any linear non-inductive configuration ranging from 1 mm to 4 mm in thickness. In other embodiments, a non-inductive antenna can consist of any linear dipole configuration ranging from about 20 microns to about 3 mm in thickness.

The antenna may also be a folded dipole antenna instead of a straight dipole antenna.

In another embodiment, the one or more non-inductive antennas may receive frequencies from about 300 MHz to about 8 GHz. In still another embodiment, the one or more non-inductive antennas may receive frequencies from about 800 MHz to about 5.8 GHz.

The signal received by an antenna is transmitted to a rectification block for rectification. The output signal of the rectifier is connected in parallel with a resistor and DC storage capacitor. The DC storage capacitor helps to smooth the rectified waveform and provide a constant power supply to a device. In one embodiment, the electronic circuitry is configured to generate a DC power supply further including a rectification circuitry and a smoothing circuitry.

The rectifier may contain one or more diodes.

In additional embodiments, the diode may be a Schottky diode, having instantaneous switching and negligible reverse recovery current. Schottky diodes are frequently used in RF detectors and mixers, allowing the use of small inductors and capacitors with greater efficiency.

Conditioning circuitry may include electronic components such as diodes, resistors and capacitors. Conditioning circuitry can use the incoming energy to provide waveforms to devices for stimulation of tissue, as well as help provide power, parameter settings and other signals to the device. The wireless power receiver may include a conditioning circuitry.

Conditioning circuitry is configured to rectify the waveform signal received by the implanted non-inductive antenna(s). Conditioning circuitry may also have charge balance microelectronics to prevent the corrosion of the contacts that are used for stimulation or for recording, and that are exposed to tissue. Conditioning circuitry may also contain a current limiter, which may limit a characteristic (for example, current or duration) of an electrical pulse to ensure that the charge per phase remains below a threshold level. To minimize reflection of the energy back from the exposed contacts into the circuitry, conditioning circuitry may further include isolation circuits to block high frequency signals.

In one embodiment, the implantable power receiver system, preferably, has an overall diameter that allows it to pass through the lumen of a standard 14 gauge needle, or smaller, such as a 16, 18, 20, or 22 gauge needle.

In other embodiments, the implantable power receiver system can be delivered into a subject's body through a needle, such as, for example, a spinal needle, no larger than gauge 18, or an endoscope, no larger than gauge 22. In still other embodiments, an outside diameter of the receiver is less than an inside diameter of a 14 gauge cannula or syringe.

In still other embodiments, the implantable power receiver can be configured within a larger housing with the sensor or circuit, or integrated with the device that the power receiver is configured to provide power to.

In yet additional embodiments, the implantable power receiver can be tethered by a wire to a body of a device that it is providing power to.

Various embodiments of a wireless implantable power receiver system have distinct advantages over traditional wired devices in regards to ease of insertion, cross-connections, small size, elimination of extension wires for transferring energy, allowing placement with minimal trauma, not requiring an implantable pulse generator (IPG), and long term effective therapy. In contrast to the present invention, larger implantable devices, such as IPG technology, may cause increased scar tissue as well as tissue reactions that may affect efficacy and safety. With the current technology, there is no longer a requirement for an IPG in order to administer a therapy.

In another embodiment, once in position, no further skin incisions or placement of extensions, receivers or implanted pulse generators are needed.

In one embodiment, the implantable power receiver may produce electrical currents capable of stimulating tissue, provide parameter settings to a device, or produce a DC voltage to power a device without a physical connection to an implantable pulse generator (IPG) or use of an inductive coil. This can be advantageous relative to designs that employ inductive coils to receive RF power through inductive coupling and then transfer the received power to a large IPG device for recharging, particularly since the large IPG device for recharging can be as large as 100 mm by 70 mm, taking up from 18 cc to over 50 cc of space in the body.

In another embodiment, the implantable power receiver may be physically integrated with a device for implantation into the body.

In another embodiment, the receiver may power one or more devices. In another embodiment, the device may include a plurality of electrodes, for example, up to 100 or more, powered by one or more receivers. In still another embodiment, the device body may hold a plurality of implantable power receivers, for example, up to 4 or more.

Various implementations also may have an associated lower overall cost compared to existing implantable devices due to the elimination of the implantable pulse generator, and this may lead to wider adoption of neural modulation therapy for patients, broader use of sensors and implanted monitors, as well as localized medication delivery mechanisms.

Devices may include stimulators, telemetry devices, sensors and body monitoring devices which monitor various physiological processes including, for example, blood pressure or other vital signs including heart rate, temperature and respiration. In other embodiments, such devices may monitor a physiological indicator such as a change of a chemical or biological molecule within an organ, tissue or the bloodstream and (optionally) may power a subsequent device to release a predefined amount of a chemical or biologic drug in response to a physiological indicator measurement.

In further embodiments, devices may include recording electrodes, glucose monitors, cochlear implant devices, cardiac devices for monitoring, pacing and defibrillation, devices for monitoring vital signs, deep brain stimulators, sensors placed externally on the body or underneath the skin, and power drug releasing or time release devices, as well as devices for recording action potentials.

In other embodiments, a wireless implantable power receiver includes one or more non-inductive antennas configured to receive radiated energy. The wireless implantable power receiver further includes electronic circuitry configured to convert the radiated energy received by the one or more non-inductive antennas into (i) a DC power supply to provide power to one or more devices; (ii) a signal to provide parameter settings to the device; (iii) a waveform to provide stimulatory signals to a tissue; or (iv) any combination thereof. The device is selected from the group consisting of: (a) a glucose monitor; (b) a cardiac device for monitoring, pacemaking or defibrillation; (c) one or more internal sensors for measuring vital signs; (d) one or more external sensors, such as EEG or ECG sensors, for measuring electrical activity; (e) microwires which measure action potential activity; (f) a time-release capsule or a drug-release device; (g) a cochlear lead; or (h) a deep brain stimulation device.

In another aspect, the implantable power receiver system includes a controller module. The controller module includes one or more non-inductive antenna(s) and one or more circuits. The non-inductive antenna(s) is configured to send a signal containing electrical energy to a remote antenna through electrical radiative coupling. The remote antenna, located externally to the implantable power receiver, is located in a module configured to create one or more electrical pulses suitable for parameter inputs to devices or to generate signals for tissue stimulation. The non-inductive antenna(s) is also configured to receive one or more signals from the remote antenna, extract a feedback signal from the one or more received signals, extract one or more parameters, and adjust an input signal to the device based upon the feedback signal. The one or more parameters of the electrical pulse may include an amplitude, duration or frequency of one or more electrical signals. In another embodiment, the receiver may provide parameter settings to a device which include frequency, amplitude and duration parameters. The implantable power receiver may provide power to the controller module.

In another aspect, the implantable power receiver communicates with one or more external devices, physically apart from the receiver, to facilitate a feedback mechanism for parameter control. For example, the implantable power receiver may also include one or more circuits for communicating information to a remote antenna of an external device, to facilitate a feedback control mechanism for parameter control. For example, the implanted power receiver may send to the second antenna a feedback signal that is indicative of the physical state of the biological process or device being monitored, and the external system may adjust parameters of the signal sent to the device through a feedback control signal.

In other embodiments, the wireless receiver system may record a physiological parameter, such as the electrical activity of the heart. In other embodiments, the wireless receiver system may contain electronic circuitry to transmit signals recorded by a device wirelessly for storage in a remote device or for processing.

In other embodiments, the wireless implantable power receiver system includes a remote system that processes signals transmitted by the receiver, to produce parameter signals, tissue stimulation signals, or both, which are transmitted to the implantable power receiver for distribution to one or more devices or tissue.

Additional embodiments of the present invention provide a method of providing power to an implanted device. The method includes providing an implantable wireless power receiver including an enclosure, and enclosure housing that houses a non-inductive antenna(s). The antenna is configured to receive, from a remote antenna and through electrical radiative coupling, an input signal containing electrical energy. The remote antenna is physically separate from the implantable receiver. One or more circuits are electrically connected to the non-inductive antenna(s) and are configured to convert the electrical energy contained in the input signal to a constant power source, preferably a DC power source. The enclosure is shaped and arranged for delivery into a subject's body through an introducer or needle.

Further embodiments of the invention provide a method of delivering electrical signals to power to the device, including enclosing the implantable wireless power receiver within the device, implanting the receiver and the device into tissue, and receiving and converting radiated energy into a DC power supply for distribution to the device, wherein the device excludes a connector.

In another embodiment, the invention may further include a method of providing parameters to a device, including receiving radiated energy by one or more non-inductive antennas and converting the radiated energy using electronic circuitry into a parameter input for distribution to the device, and delivering the parameter input to the device, wherein the device excludes a connector.

In still further embodiments, the invention further includes a method of providing stimulatory waveforms to tissue, including receiving radiated energy from one or more non-inductive antennas and converting the radiated energy using electronic circuitry into an electrical waveform suitable for tissue simulation, delivering the waveform to the device for distribution into the tissue, and stimulating the tissue, wherein the device excludes a connector.

Neural tissue associated with the spinal column includes the spinothalamic tracts, dorsal horn, dorsal root ganglia, dorsal roots, dorsal column fibers, and peripheral nerve bundles leaving the dorsal column or brainstem.

The wireless implantable power receiver system may (optionally) include electronic circuitry to transmit recorded signals from the device to which it provides power, to a remote system for storage, processing, or both. The remote system processes received signals to produce parameter signals, tissue stimulation signals, or any combination thereof, which are then transmitted to the implantable power receiver for distribution to one or more devices.

FIG. 1 depicts an example of an implantable power receiver 110 powering stimulation or recording electrodes 100. The electrodes 100 are represented by solid black rectangles at the distal end of the device 120. The receiver 110 is represented by the hatched rectangle at the proximal end of the device 120. In one embodiment, the device 120 may have two electrodes 100 powered by the receiver 110. In another embodiment, the device 120 may have a plurality of electrodes 100, for example, up to 100 or more, powered by one or more receivers 110. In yet another embodiment, a single power receiver 110 is embedded within the device body 120. In still another embodiment, the device body 120 may hold a plurality of implantable power receivers 110. E.g., up to four, more than four, two, etc.

Figure 2A:
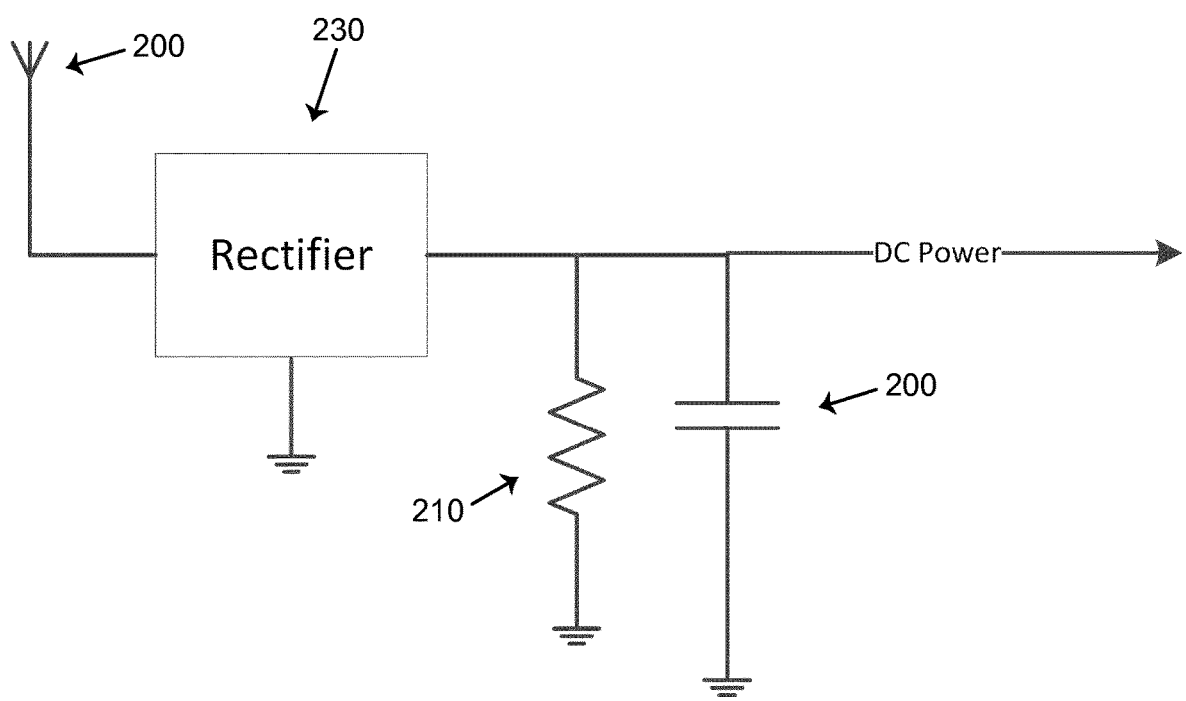
FIG. 2A illustrates an example of internal circuitry for the implantable power receiver system to generate DC power, according to an exemplary embodiment.
Figure 2B:
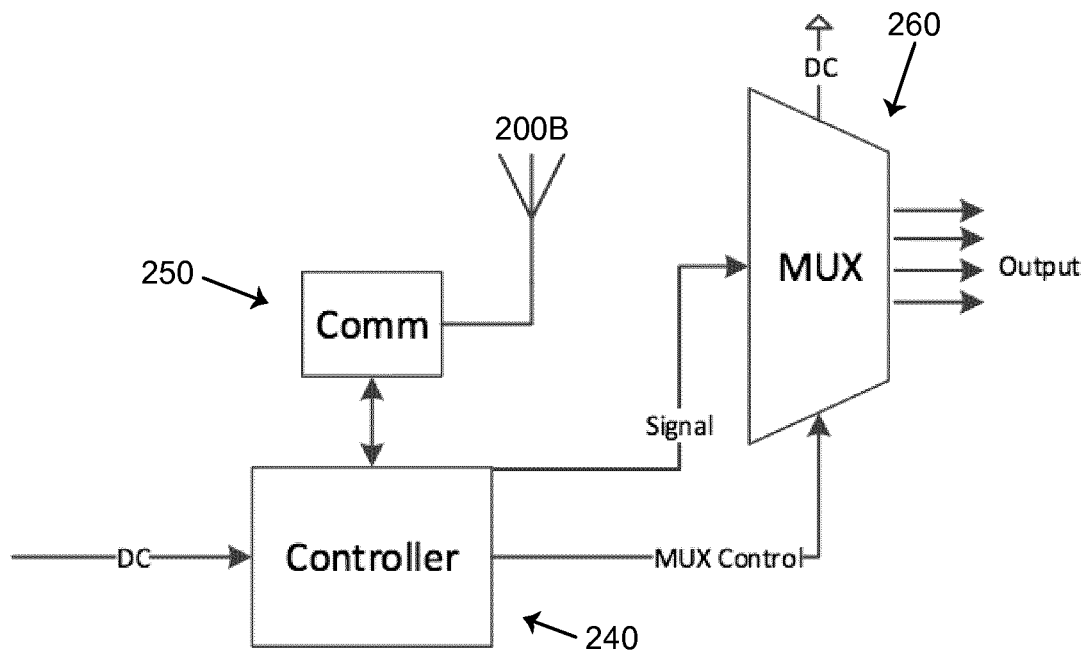
FIG. 2B illustrates an example of internal circuitry for the implantable power receiver system to communicate with a device, according to an exemplary embodiment.
Figure 2C:
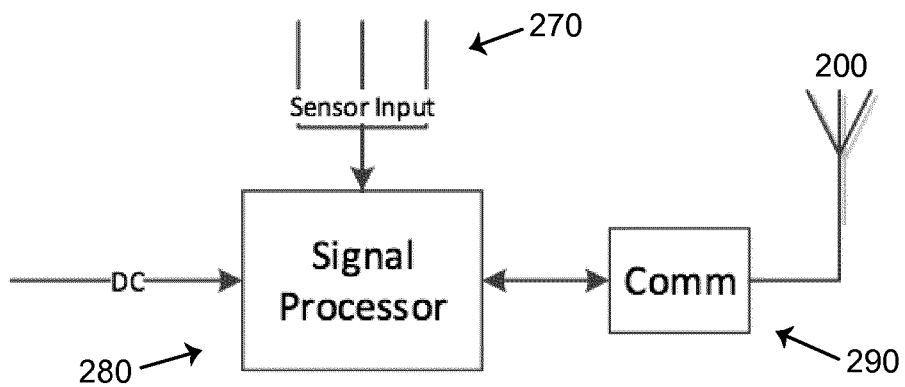
FIG. 2C illustrates another example of internal circuitry for the implantable power receiver system to communicate with a device, according to an exemplary embodiment.

FIGS. 2A-2C depict block diagrams for the implantable power receiver power generation and parameter control, according to some exemplary embodiments.

In FIG. 2A, a signal is received by the implanted antenna 200 (e.g., non-inductive antenna) and the received energy (e.g., power and modulations representative of data, just power, just modulations representative of data, etc.) is transmitted to a rectifier circuit 230. The rectifier circuit can provide for rectification of up to 10 Volts DC power per receiver, according to an exemplary embodiment. With reference to the medical device of FIG. 1, the voltage output may be configured depending on the depth of the implanted receiver within tissue. The same general configuration may utilized for multiple receivers. Such multiple receivers can be placed in parallel and the output power daisy chained to create a larger maximum power supply to one or more devices. The output signal of the rectifier 230 may be connected in parallel with a resistor 210 and time release capacitor 220, providing smoothing circuitry. In other embodiments, the smoothing circuitry may contain one or more resistors and one or more capacitors. The capacitor 220 serves to smooth the rectified waveform and help provide a continuous supply of power to a device. The rectifier 230 and smoothing circuitry are part of the conditioning circuitry. It should be appreciated that capacitor 220 should not be considered a long term power supply such as a battery. As such, FIG. 2A advantageously does not include a battery for powering the medical device attached to the circuit of FIG. 2A.

FIG. 2B shows a controller 240 which receives, as an input, the DC power supply, from FIG. 2A. In other words, the energy received at antennas 200 can be used to provide power to the signal processing electronics and controller of FIG. 2B. The energy received at non-inductive antennas 200 can contain modulations (e.g., AM, FM, etc.) representative of data signals.

In some embodiments, the received signal by a supplemental antenna 200B can be processed by a communication block 250 which is connected to the controller 240. In other embodiments, the controller 240 can pass the received DC power to the communications block 250 for demodulation and passing back to the controller.

In addition to supplying the connected device with DC power, the controller 240 can generates a data signal, which may be based upon the received energy from the DC Power and/or from energy received at antenna 200. The DC power can be distributed to the medical device. In a further embodiment, in cases in which the receiver is connected to multiple devices or multiple tissue sites, the design configuration may contain a multiplexer 260 to deliver a designated signal to a specific device or tissue. The controller 240 may also supply a MUX control signal, to select a particular output channel of the multiplexer 260. Additionally, the output of the controller 240 can be transmitted to a remote site for storage or further processing.

In still another embodiment, FIG. 2C shows a configuration in which the system (optionally) includes a signal processing block 280. The signal processing block 280 is powered by the power generating circuitry, and may also receive an input from a non-inductive antenna(s) 200. The received signal by the antenna is processed by a communication block 290 which is connected to the signal processor 280. Sensor input 270 may be fed into the signal processing unit 280, and once processing completes, the output of the processing unit 280 may be transmitted to a remote storage or processing site.

The various configurations shown in FIG. 2A-2C may be used with medical stimulation or monitoring devices powered by the implantable power receiver. It is important to note that in FIGS. 2B and 2C, the DC power may be supplied by any suitable power source or by the energy harvesting receiver of FIG. 2A.

Figure 3:
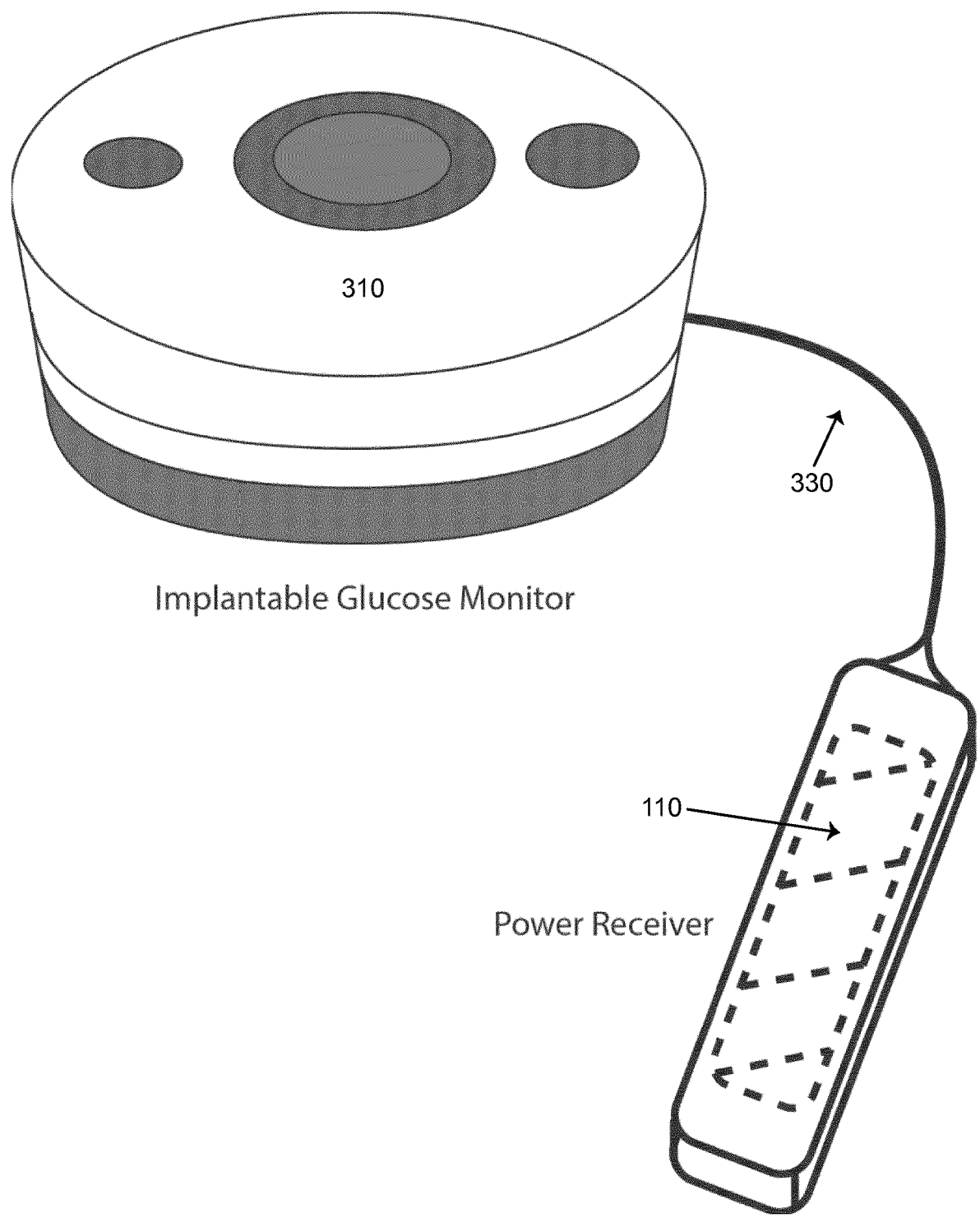
FIG. 3 illustrates the implantable power receiver system connected to an implantable glucose monitoring device, according to an exemplary embodiment.

FIG. 3 depicts another embodiment of one or more implantable power receivers 110 that can be attached by a wire tether 330 to send power and data instructions to a sensor system. In this particular embodiment, the receiver 110 is connected to an implantable glucose monitor 310 which includes a sensor for continually monitoring blood glucose levels. In this configuration, the power receiver 110 is represented by the hatched rectangle.

Figure 4:
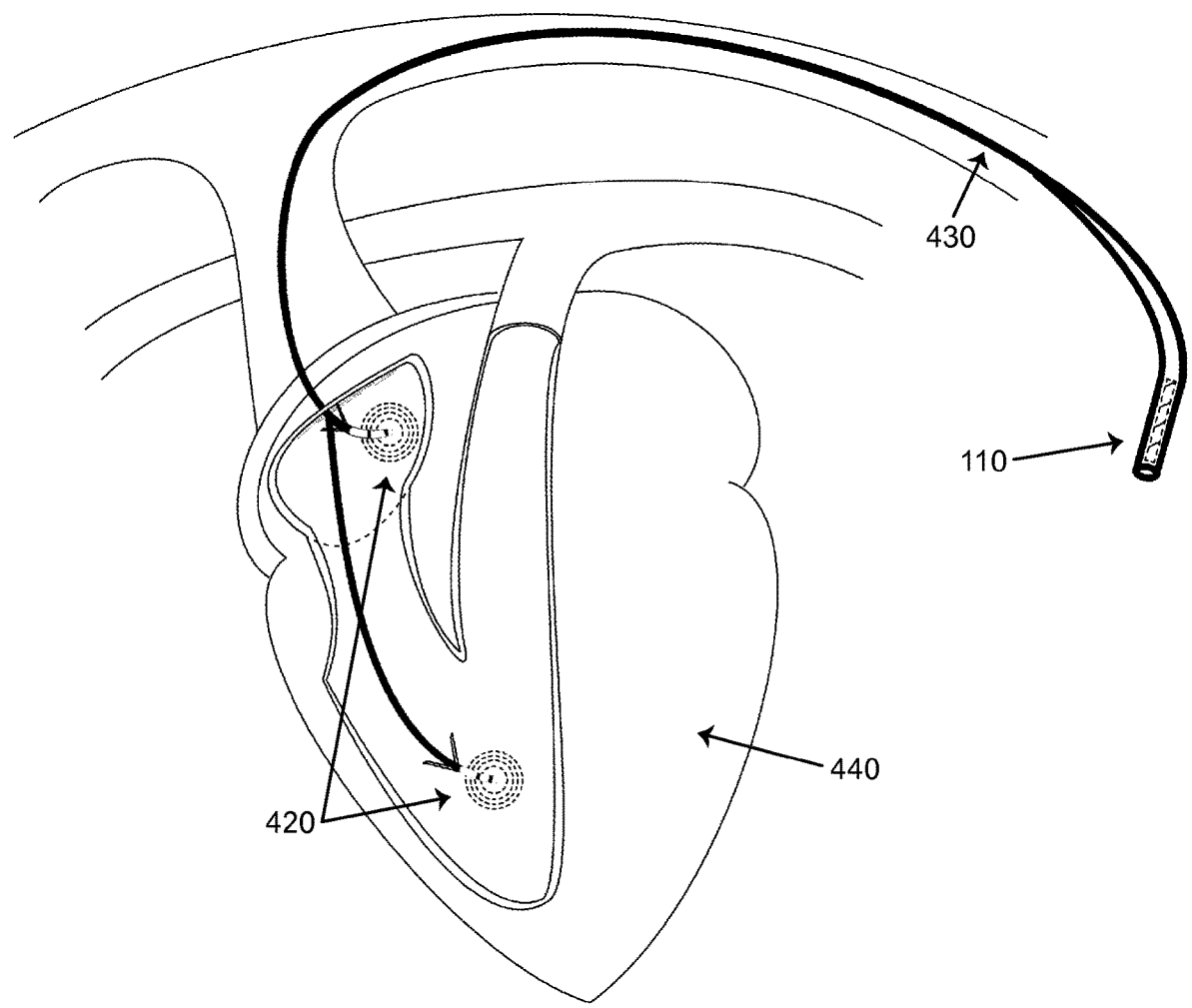
FIG. 4 illustrates the implantable power receive system placed within the heart through a catheter run through an artery for recording vital signs, according to an exemplary embodiment.

FIG. 4 depicts another embodiment, in which one or more implantable power receivers 110 can be placed within the heart 440 through a catheter 430 run through an artery. In this example, a receiver 110 is shown in the proximal end of the catheter 430 and one or more sensors 420 are shown attached to the heart 440. In this example, the receiver 110 is shown as a hatched rectangle. The receiver 110, once placed, may be used for recording or transmitting vital signs, powering of sensors, and providing signals, for example, such as pacing or defibrillation signals, for distribution to the tissue of the heart 440. Examples of vital signs that can be monitored by sensors that are powered by these implantable receivers 110 include heart rate, body temperature or blood pressure. In other embodiments, the receiver 110 may power sensors which measure both systolic and diastolic blood pressure. In addition, the system may monitor a chemical or biological signal, such as a change in concentration of a molecule found within a tissue, an organ or within the bloodstream.

In another embodiment, the implantable receiver 110 may be within a lead body connected to an electrode array that is placed into a descending branch of the left or right pulmonary artery (PA). The lead body with the implantable receiver 110 may be marked with a material to allow visualization, such as through fluoroscopy, during placement.

In addition to sensors, the implantable receiver 110 may be used to power circuitry which transmits measured information to an external device for processing and storage.

In another embodiment, the implantable receiver 110 is connected to leads, which are flexible, insulated wires implanted into the heart 440 to monitor the heart's electrical activity. For example, a typical procedure would involve placing one or more leads into the heart 440, such as the right atrium, the right ventricle, or both. In another embodiment, the leads may be placed on or in close proximity to the sinoatrial node.

In one embodiment, the implantable receiver system may monitor the electrical activity of the heart 440 through the implanted leads, and deliver electrical signals to the heart muscle, if the pace becomes too slow or too fast. In another embodiment, pacing and defibrillation may be performed in the right ventricle, in the right atrium, or both. In another embodiment, pacing may be performed on a time scale commensurate with the rate of beating of the heart 440.

In yet another embodiment, the implantable receiver system stores parameters for maintaining certain "pacing conditions." The receiver 110 may also receive parameter signals for pacing or defibrillation.

Figure 5:
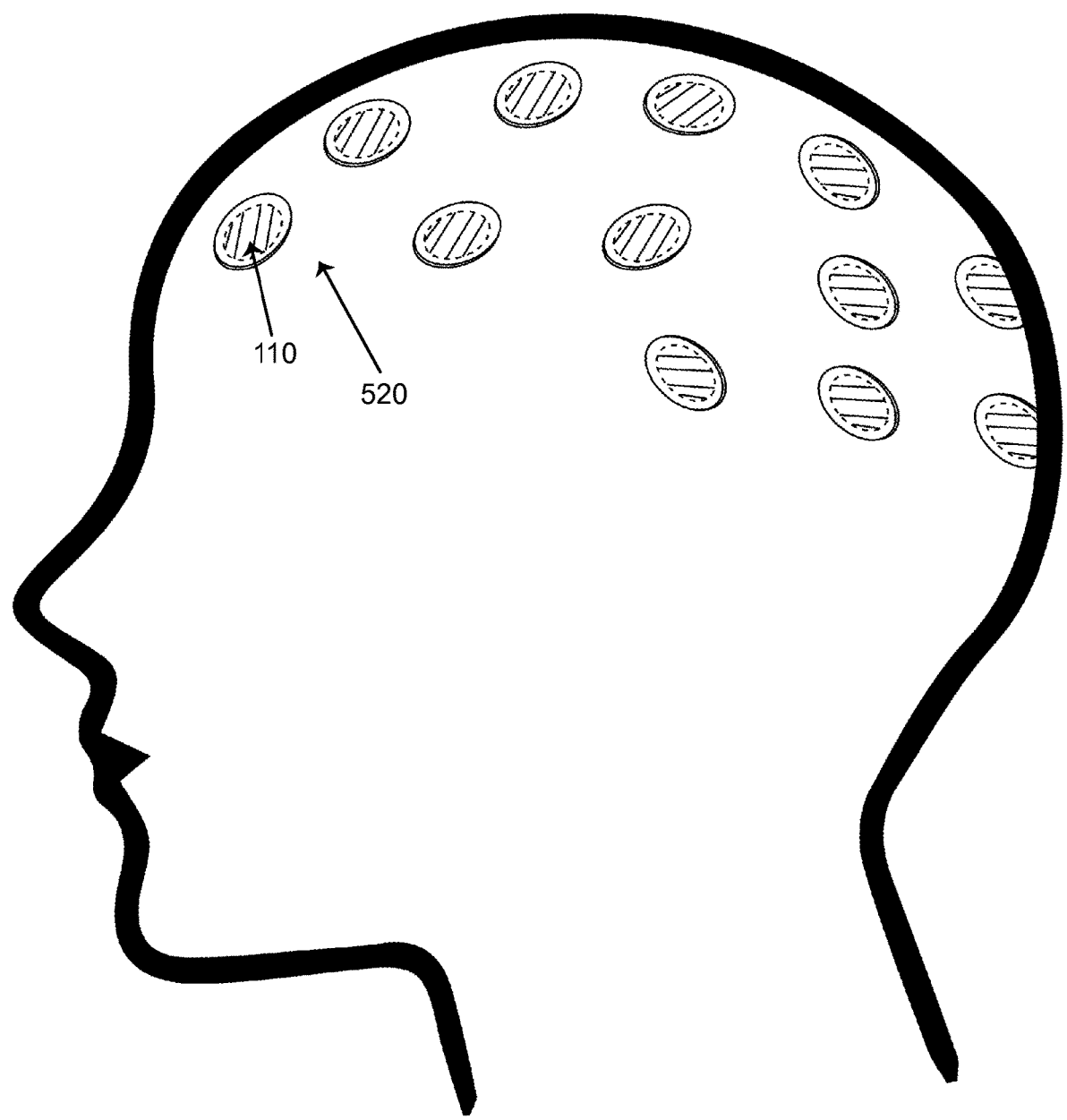
FIG. 5 illustrates small EEG pads that include the implantable power receiver system placed on the surface of the head or implanted under the skin, according to an exemplary embodiment.

FIG. 5 illustrates another embodiment of the implantable power receiver 110. The receiver 110 can be placed in a plurality of small EEG pads 520 on the surface of the head. In other embodiments, the receiver 110 may also be placed in an ECG sensor (not shown) or implanted under the skin, for example, as part of an ECG wireless sensor system.

This figure illustrates a receiver 110, shown as a hatched circle, connected to a sensor, such as an EEG pad 520, placed on the surface of a head. The receiver 110 provides power to the EEG sensor 520 as well as transmits recorded signals of the electrical activity of the brain to an external device for processing or display on a monitor.

In yet another embodiment, the receiver 110 may be connected to an ECG device to diagnose disorders such as cardiac arrhythmias. Such arrhythmias may result from abnormalities in electrical activity of the sinus node, from irregular beats in the chambers of the heart, abnormal electrical pathways in the heart or irregularities from underlying coronary artery disease. Such disorders may include, but are not limited to, for example, sinus arrhythmia, sinus tachycardia, sinus brachycardia, sick sinus syndrome, premature atrial contraction, supraventricular tachycardia, Wolfe-Parkinson-White syndrome, atrial flutter and atrial fibrillation, premature ventricular complexes, ventricular tachycardia and ventricular fibrillation.

Figure 6:
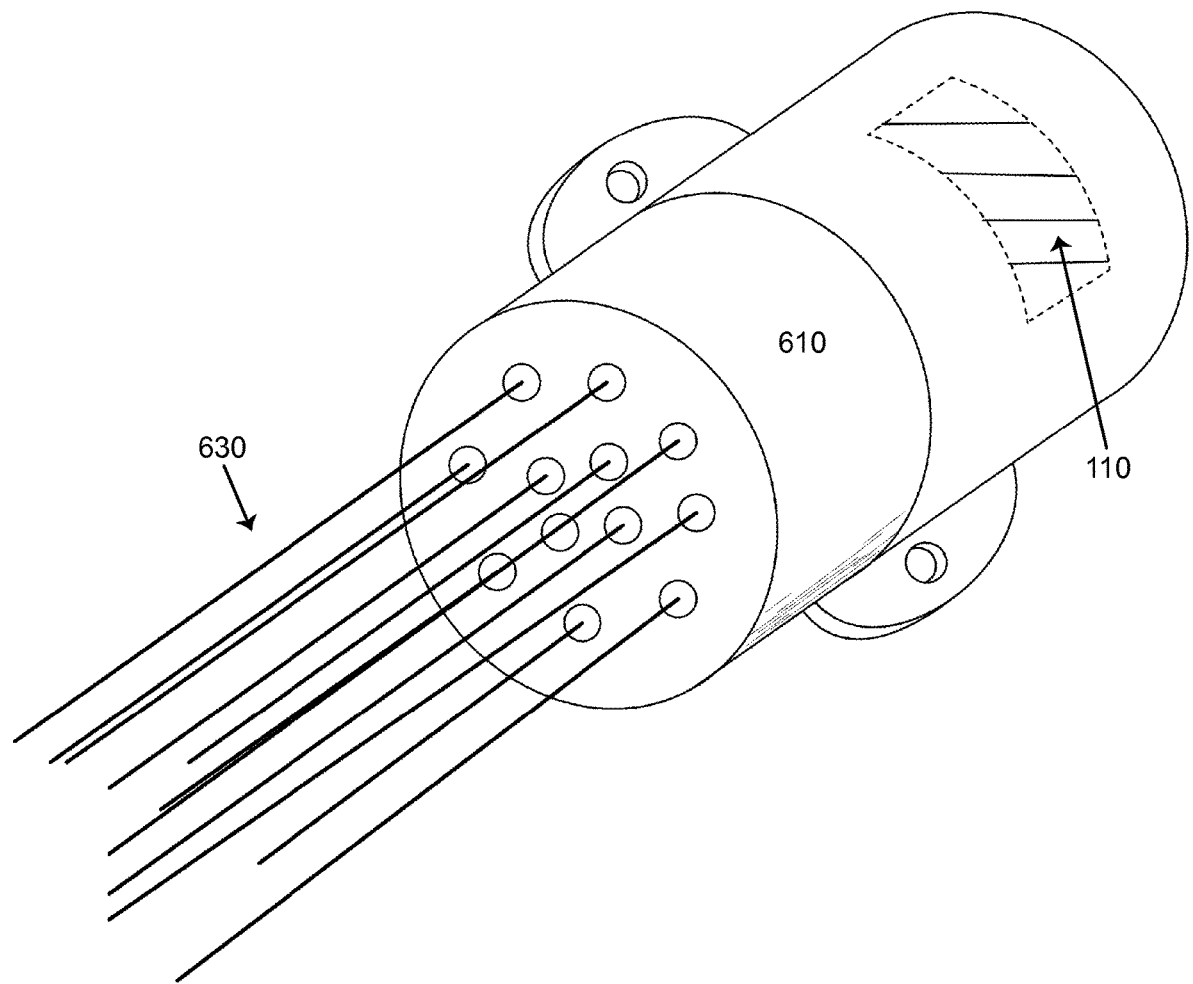
FIG. 6 illustrates fine microwaves powered by the implantable power receiver system to record action potential activity from target tissue, according to an exemplary embodiment.

FIG. 6 illustrates another embodiment of the implantable power receiver 110. In this example, one or more fine microwires 630 may be powered by the receiver 110 to record action potential activity from targeted tissue, such as brain tissue or direct nerve fascicles. The figure illustrates a receiver 110, shown as a hatched rectangle, connected to a device 610 which extrudes fine microwires 630.

In one embodiment, the microwires 630 can be made from materials comprised of metal, conducting polymers, or other materials with conductive properties.

In another embodiment, the microwires 630 may be implanted for continuous recording of electrophysiological activity. The receiver 110, in this case, may also transmit the recorded signal to an external device for storage and processing.

Figure 7:
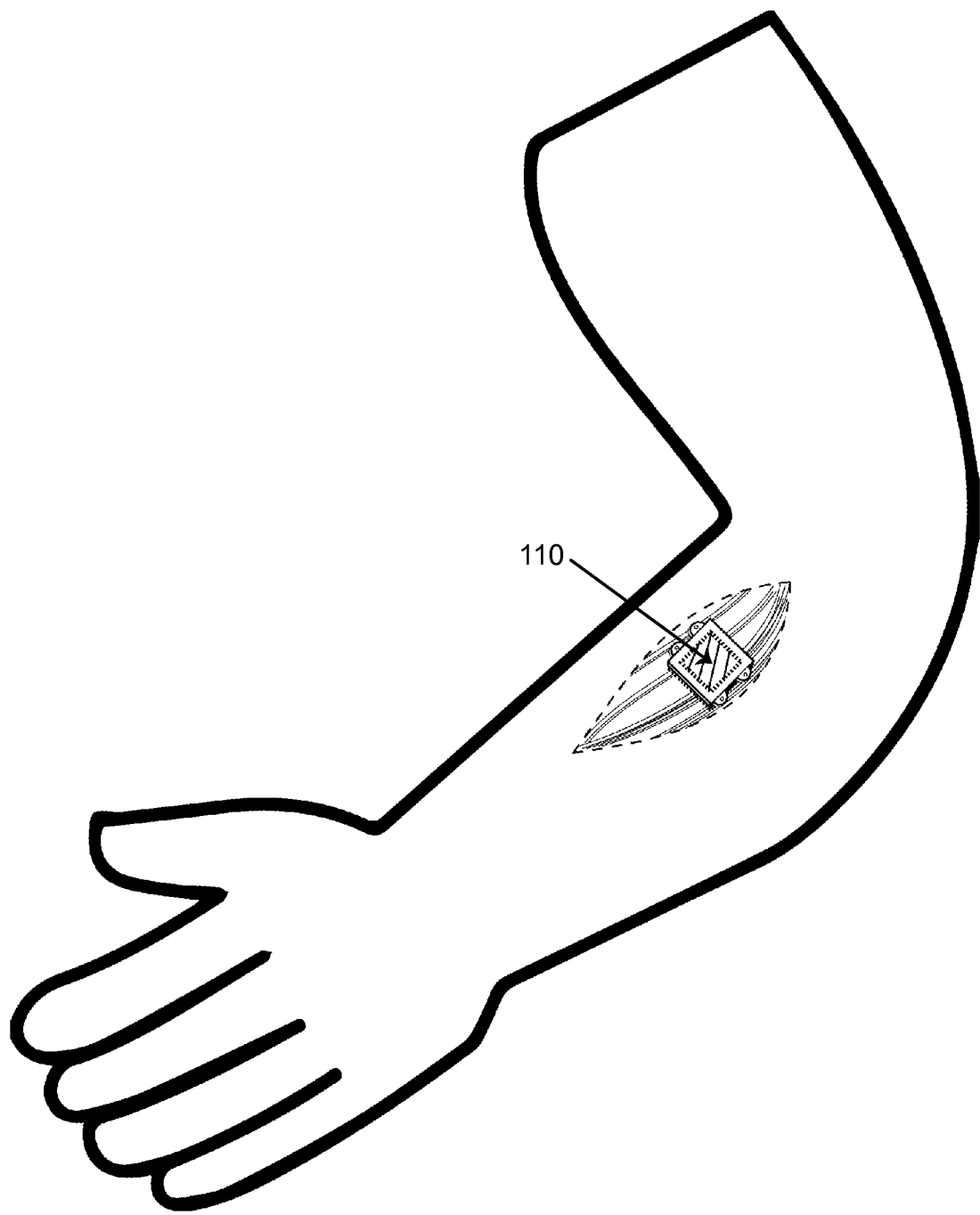
FIG. 7 illustrates the implantable power receiver system placed under the skin at a location within a body to provide energy to activate tissue, to power an implanted sensor, or to control drug release from implanted time-release capsules, according to an exemplary embodiment.

FIG. 7 illustrates another embodiment of the implantable power receiver 110. In this embodiment, a small implanted power receiver 110 may be placed under the skin at any location within the body, to provide power, parameters to a device, energy to activate a tissue, or any combination thereof. The figure illustrates a receiver 110, shown as a hatched rectangle, attached to a sensor, implanted under the skin.

In another embodiment, the receiver 110 may be implanted under the skin to power another component, to control drug release from implanted time-release capsules or a drug pump unit.

Figure 8:
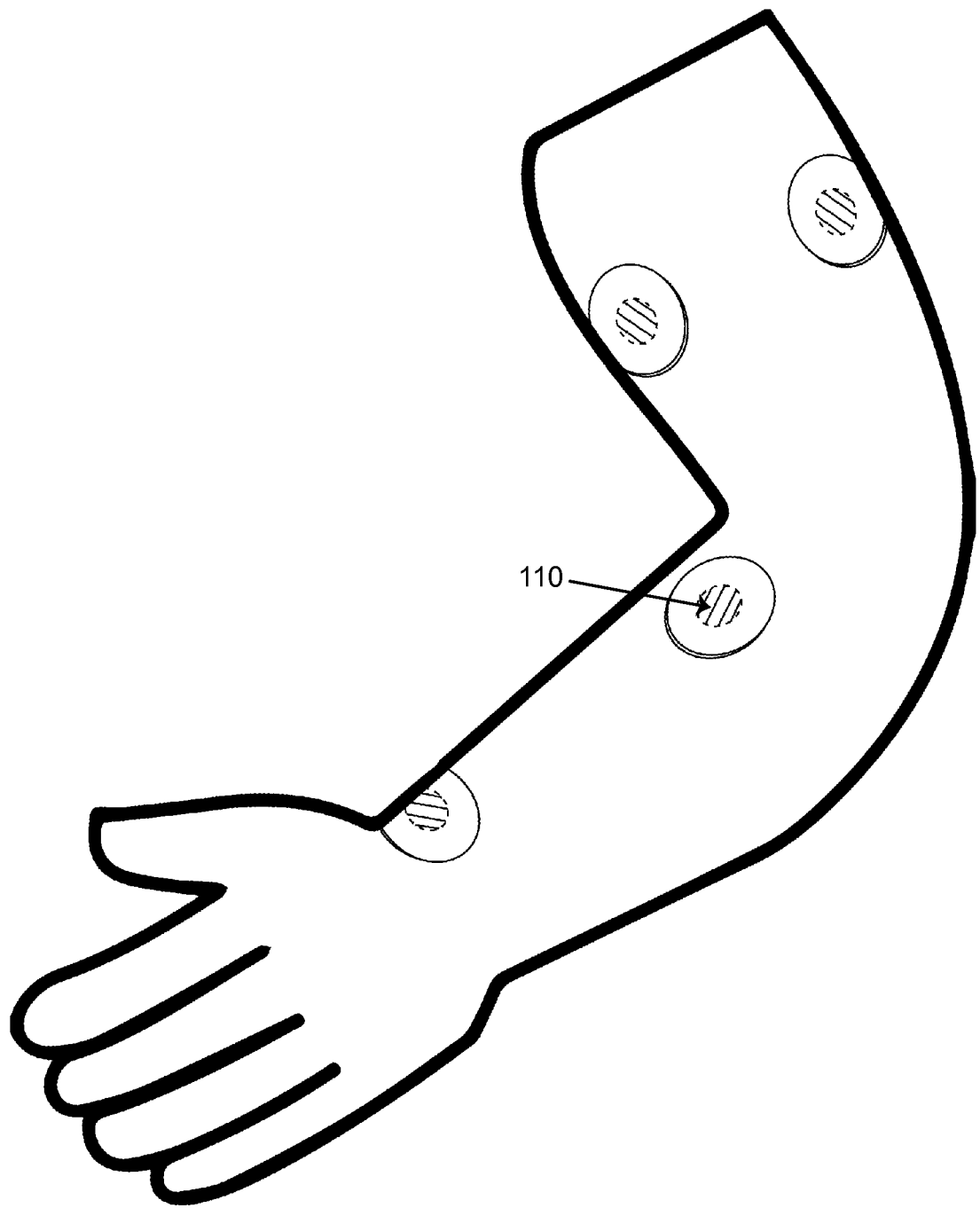
FIG. 8 illustrates implantable power receiver systems placed externally on the tissue of the body and remotely powered to provide stimulation signals or provide power to other sensory units, according to an exemplary embodiment.

FIG. 8 illustrates another embodiment of the implantable power receiver 110. In this embodiment, the receiver 110 may be placed externally on tissue and remotely powered to provide stimulation signals or power to other sensory units. In another embodiment, the receiver 110 can be externally placed on tissue to control medication eluding devices. The medication eluding devices may be implanted into the human body. The receiver 110 is shown as a hatched circle.

Figure 9:
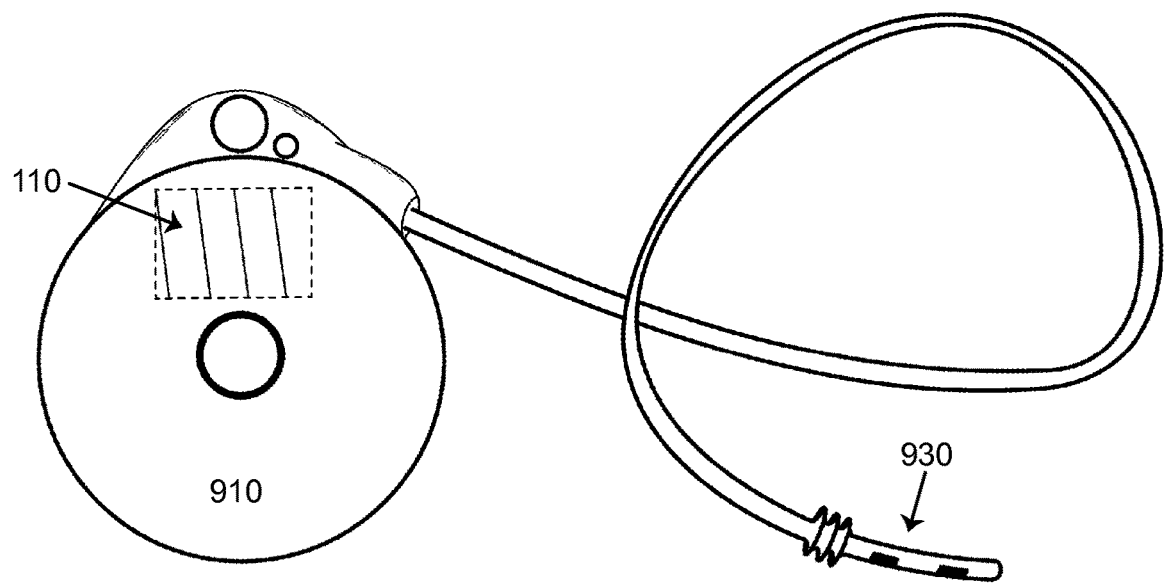
FIG. 9 illustrates the implantable power receiver system tethered to a drug pump unit for powering the release of medications, according to an exemplary embodiment.

FIG. 9 illustrates an embodiment, in which one or more implantable power receivers 110 are tethered to a drug pump unit 910 (round device) for powering and transmitting data to control the release of medications. In addition to providing power, the receiver 110 may also deliver signals to the drug pump unit 910 to release prescribed amounts of medication. The receiver 110 is shown as a hatched rectangle within the body of the drug pump device 910.

A drug pump unit 910 may contain a pump (round device) for storing and delivering medication as well as a catheter 930, or thin, flexible tubing, for delivering medication to a particular location. The drug pump unit may release the drug via (i) a nonprogrammable fixed-rate method in which the dose may be changed by adjusting the concentration of the drug or (2) a programmable method in which a single or a timed dose may be administered, or the infusion rate may be adjusted.

The receiver 110 may provide power, parameters to the drug pump unit to control the amount of and rate of release of the medication.

In another embodiment, a microchip with one or more reservoirs is implanted into tissue. The reservoirs are storage units for pharmaceuticals. The receiver 110 may receive radiated energy and convert this into a power supply and parameter settings for triggering the opening of a particular reservoir chamber for distribution of drugs.

Figure 10:
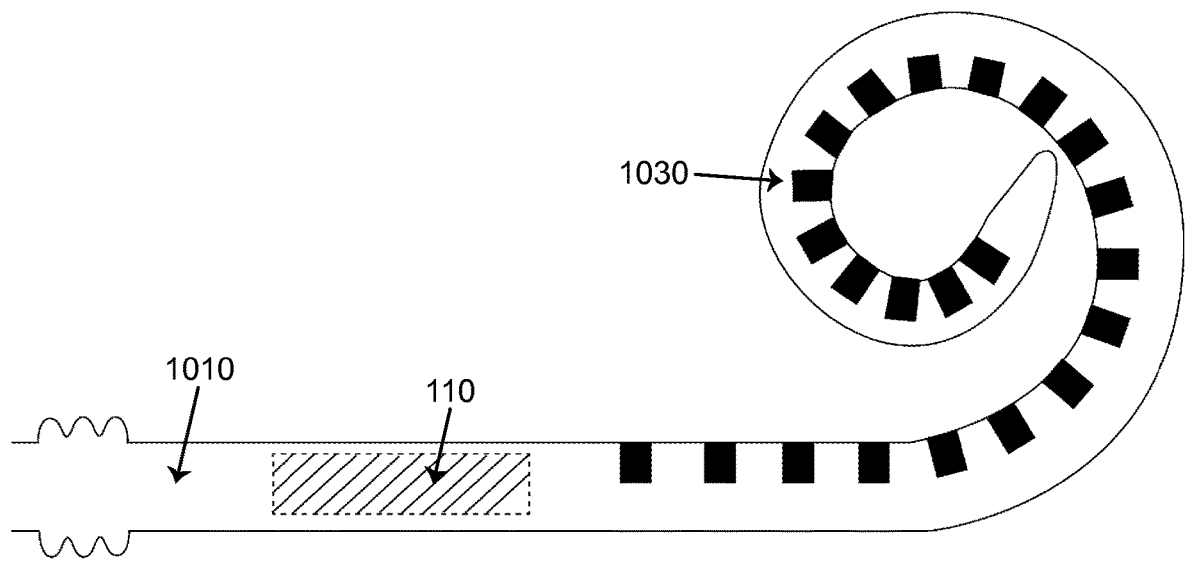
FIG. 10 illustrates the implantable power receiver system tethered to a cochlear lead to power a hearing aid device without an implanted battery, according to an exemplary embodiment.

FIG. 10 illustrates another embodiment, disclosed herein, of the implantable power receiver 110. In this embodiment, the receiver 110 is tethered to a cochlear lead 1010 to power a hearing aid device, without using an implanted battery. The cochlear lead 1010 may have one or a plurality of electrodes 1030, along a length of a flexible body. In this figure, the receiver 110 is shown as a hatched rectangle within the body of the device and the electrodes 1030 are shown as solid rectangles extending along the body to the distal end of the device.

The receiver 110 may provide power and stimulatory signals to the cochlear lead 1010. The cochlear lead 1010 has a plurality of electrodes 1030 which may be configured to stimulate an auditory nerve from within a cochlea.

Cochlear systems may have an externally located transmitter that transmits sound information to the internally located position of the device, a cochlear lead 1010, a microphone to capture sound information in the environment, and a signal processing unit to convert the sound to a signal to be transmitted to the cochlear lead 1010.

In one embodiment of the present invention, the cochlear lead 1010 has an implantable power receiver 110 that receives the power and converts this into an electrical signal to power the electronics of the cochlear system. The power receiver 110 also converts the received signal by the noninductive antenna(s) to a digital data set instruction.

In other embodiments, the present invention may improve the form factor of the implanted cochlear lead 1010.

Figure 11:
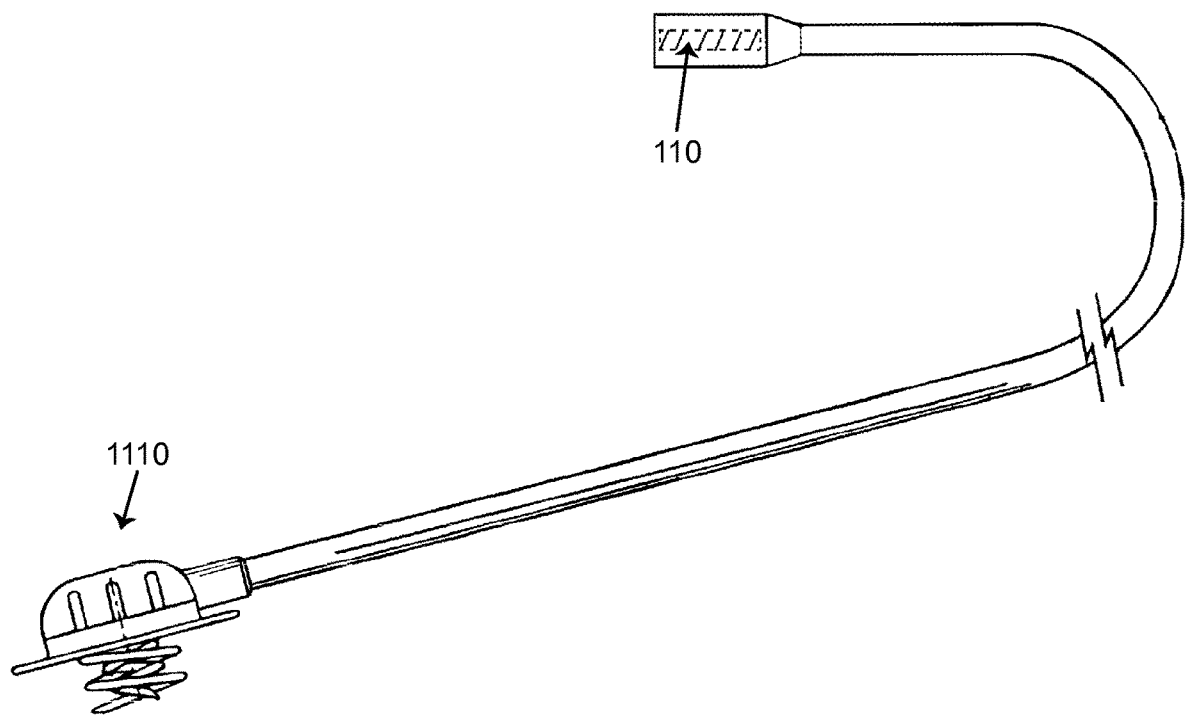
FIG. 11 illustrates the implantable power receiver system tethered to a screw lead configuration used for brain stimulation, according to an exemplary embodiment.

FIG. 11 illustrates another embodiment of the implantable power receiver 110. In this embodiment, the receiver 110 may be tethered to a screw lead configuration 1110 used for brain stimulation. The receiver 110, as shown, is located proximal to the distal end of the screw lead configuration 1110. The receiver 110 is shown as a hatched rectangle.

Deep brain stimulation (DBS) systems may include a lead, with one or more electrodes, a neurostimulator (for example, an IPG) with microelectronics and a power supply. The lead is placed within the brain.

DBS may be useful for various movement disorders, including but not limited to, for example, Parkinson's disease, essential tremor, arm tremors and dystonia. Additionally, DBS systems can be used to treat a variety of neurological conditions, including but not limited to, for example, Tourette syndrome, obsessive-compulsive disorder, and major depression.

Pulses of electrical energy can be used to interfere with and block electrical signals that cause movement disorders.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. A wireless implantable power receiver, comprising:
   a non-inductive antenna configured to receive, without inductive coupling, electrical energy radiated from outside a subject; and
   electronic circuitry configured to convert the radiated electrical energy as received, without inductive coupling, by the non-inductive antenna to create one or more electrical pulses to drive an implantable medical stimulation device with voltages higher than 2V sufficient for the implantable medical stimulation device to deliver electrical currents suitable for stimulating tissue surrounding the implantable medical stimulation device,
   wherein the electronic circuitry comprises:
      a bridge rectifier including two parallel pairs of diodes, a first pair of diodes connected anode-to-anode in series, a second pair of diodes connected cathode-to cathode in series,
   wherein the wireless implantable power receiver is a stand-alone device that is distinct and different from the implantable medical stimulation device, and
   wherein the implantable medical stimulation device is powered by the converted electrical energy such that the implantable medical stimulation device does not require battery power or wired power from outside the subject.

2. The wireless implantable power receiver of claim 1, wherein the electronic circuitry further comprises a rectification circuitry and a smoothing circuitry.

3. The wireless implantable power receiver of claim 2, wherein the rectification circuitry and the smoothing circuitry are passive.

4. The wireless implantable power receiver of claim 3, wherein the rectification circuitry further comprises one or more diodes.

5. The wireless implantable power receiver of claim 3, wherein the smoothing circuitry further comprises one or more resistors and one or more capacitors.

6. The wireless implantable power receiver of claim 1, wherein the electronic circuitry provides up to 10 Volts DC power to the implantable medical stimulation device.

7. The wireless implantable power receiver of claim 1, wherein the wireless implantable power receiver is physically integrated within an enclosure of the implantable medical stimulation device.

8. The wireless implantable power receiver of claim 1, wherein the electronic circuitry delivers power to a plurality of sensors of the medical stimulation device.

9. The wireless implantable power receiver of claim 1, wherein the wireless implantable power receiver is sized and shaped for passing through an inner lumen of a needle no larger than 13 gauge.

10. The wireless implantable power receiver of claim 1, wherein the first pair of diodes are connected at a first juncture, wherein the second pair of diodes are connected at a second juncture, and wherein the electronic circuitry further comprises: one or more shunt resistors and one or more capacitors disposed between the first juncture and the second juncture.

11. A wireless implantable power receiver for a medical stimulation device implanted in a subject, comprising:
   a non-inductive antenna configured to receive, without inductive coupling, electrical energy radiated from outside the subject; and
   electronic circuitry configured to convert the radiated electrical energy as received, without inductive coupling, by the non-inductive antenna to power the medical stimulation device implanted in the subject with voltages higher than 2V and to provide parameter settings to the medical stimulation device such that the medical stimulation device delivers electrical currents suitable for stimulating tissue surrounding the medical stimulation device,
   wherein the electronic circuitry comprises:
      a bridge rectifier including two parallel pairs of diodes, a first pair of diodes connected anode-to-anode in series, a second pair of diodes connected cathode-to cathode in series,
   wherein the wireless implantable power receiver is a stand-alone device that is distinct and different from the medical stimulation device, and
   wherein the medical stimulation device is powered by the converted electrical energy such that the medical stimulation device does not require battery power or wired power from outside the subject.

12. The wireless implantable power receiver of claim 11, wherein the receiver is enclosed in a housing shared by the medical stimulation device.

13. The wireless implantable power receiver of claim 11, wherein the receiver comprises a conditioning circuitry configured to condition the received electrical energy.

14. The wireless implantable power receiver of claim 11, wherein at least one of the non-inductive antennas comprises a conductive trace on one of the circuits.

15. The wireless implantable power receiver of claim 11, in which at least one of the non-inductive antennas is fabricated as a conductive wire connected to one of the circuits.

16. The wireless implantable power receiver of claim 11, in which one or more non-inductive antennas have a length ranging from about 100 microns to about 10 cm.

17. The wireless implantable power receiver of claim 11, in which one or more non-inductive antennas have a thickness ranging from about 20 microns to about 3 mm.

18. The wireless implantable power receiver of claim 11, in which one or more non-inductive antennas receive frequencies from about 300 MHz to about 8 GHz.

19. The wireless implantable power receiver of claim 11, in which the parameter settings distributed to the medical stimulation device include frequency, amplitude and duration parameters.

20. The wireless implantable power receiver of claim 11, wherein the electronic circuitry is further configured to transmit signals recorded by the medical stimulation device to a remote system for storage or processing.

21. The wireless implantable power receiver of claim 20, wherein the electronic circuitry is further configured to transmit signals recorded by the medical stimulation device to a remote system such that the remote system, in response to the transmitted signals, produces parameter signals, tissue stimulation signals, or both, and then transmits the same to the implantable power receiver for distribution to elements of the medical stimulation device.

22. A system comprising a plurality of wireless implantable power receivers of claim 11, in which each wireless implantable power receiver is arranged in series, with respect to one another, to produce a power supply that is greater than 10 Volts DC power.

23. The wireless implantable power receiver of claim 11, wherein the medical stimulation device comprises microwires which measure action potential activity.

24. The wireless implantable power receiver of claim 11, wherein the wireless implantable power receiver is sized and shaped for passing through an inner lumen of a needle no larger than 13 gauge.

25. The wireless implantable power receiver of claim 11, wherein the first pair of diodes are connected at a first juncture, wherein the second pair of diodes are connected at a second juncture, and wherein the electronic circuitry further comprises: one or more shunt resistors and one or more capacitors disposed between the first juncture and the second juncture.

26. A medical device system, comprising:
an implantable medical stimulation device; and
a wireless implantable power receiver comprising:
(a) a non-inductive antenna configured to receive, without inductive coupling, electrical energy radiated from outside a subject; and
(b) electronic circuitry configured to convert the radiated electrical energy as received, without inductive coupling, by the non-inductive antenna to power the implantable medical stimulation device implanted in the subject with voltages higher than 2V sufficient for the implantable medical stimulation device to deliver electrical currents suitable for stimulating tissue surrounding the medical stimulation device,
wherein the electronic circuitry comprises:
a bridge rectifier including two parallel pairs of diodes, a first pair of diodes connected anode-to-anode in series, a second pair of diodes connected cathode-to-cathode in series,
wherein the wireless implantable power receiver is a stand-alone device that is distinct and different from the medical stimulation device, and
wherein the medical stimulation device is powered by the converted electrical energy such that the medical stimulation device does not require battery power or wired power from outside the subject.

27. The medical device system of claim 26, wherein the medical stimulation device s includes one or more electrodes configured to apply one or more electrical pulses to a neural tissue associated with the subject's spinal column.

28. The medical device system of claim 26, in which the electronic circuitry further comprises a rectification circuitry and a smoothing circuitry.

29. The medical device system of claim 28, in which the rectification circuitry and the smoothing circuitry are passive.

30. The medical device system of claim 29, in which the rectification circuitry further comprises one or more diodes.

31. The medical device system of claim 29, in which the smoothing circuitry further comprises one or more resistors and one or more capacitors.

32. The medical device system of claim 26, wherein the wireless implantable power receiver is configured to provide up to 10 Volts DC power.

33. The medical device system of claim 26, wherein the wireless implantable power receiver is physically integrated within an enclosure of the medical stimulation device.

34. The medical device system of claim 26, wherein the wireless implantable power receiver is tethered by one or more wires to the medical stimulation device.

35. The medical device system of claim 26, wherein the wireless implantable power receiver provides power to a plurality of sensors within the medical stimulation device.

36. The medical device system of claim 26, wherein the wireless implantable power receiver is sized and shaped for passing through an inner lumen of a needle no larger than 13 gauge.

37. A method of delivering electrical signals to power to an implantable medical stimulation device, comprising:
enclosing an implantable wireless power receiver within the implantable medical stimulation device such that the implantable wireless power receiver is connected to the implantable medical stimulation device, wherein the implantable wireless power receiver is a stand-alone device that is distinct and different from the implantable medical stimulation device;
implanting the implantable wireless power receiver and the implantable medical stimulation device into tissue in a subject such that a one or more non-inductive antennas on the implantable wireless power receiver receives, without inductive coupling, electrical energy radiated from outside the subject, and electronic circuitry on the implantable wireless power receiver converts the radiated electrical energy as received, without inductive coupling, by the one or more non-inductive antennas to power the implantable medical stimulation device with voltages higher than 2V sufficient for the implantable medical stimulation device to deliver electrical currents suitable for stimulating tissue surrounding the implantable medical stimulation device, wherein the electronic circuitry comprises:
a bridge rectifier including two parallel pairs of diodes, a first pair of diodes connected anode-to-anode in series, a second pair of diodes connected cathode-to cathode in series; and operating the medical stimulation device using the converted electrical energy without requiring battery power or wired power from outside the subject.

38. The method of claim 37, further comprising:
extracting a parameter input from the received electrical energy; and
delivering the parameter input to the medical stimulation device.

39. The method of claim 38, wherein the parameter input has at least three different possible values.

40. The method of claim 37, further comprising:
generating an electrical waveform suitable for tissue simulation solely using the received electrical energy; and
delivering the electrical waveform to the medical stimulation device for distribution into the tissue, and stimulating the tissue.

41. The method of claim 37, further comprising:
passing the implantable wireless power receiver through an inner lumen of a needle no larger than 13 gauge.

42. The method of claim 37, wherein the first pair of diodes are connected at a first juncture, wherein the second pair of diodes are connected at a second juncture, and wherein the electronic circuitry further comprises: one or more shunt resistors and one or more capacitors disposed between the first juncture and the second juncture.

* * * * *

UNITED STATES PATENT AND TRADEMARK OFFICE
CERTIFICATE OF CORRECTION

PATENT NO. : 10,994,149 B2
APPLICATION NO. : 14/214241
DATED : May 4, 2021
INVENTOR(S) : Laura Tyler Perryman and Chad Andresen Page 1 of 1

It is certified that error appears in the above-identified patent and that said Letters Patent is hereby corrected as shown below:

In the Claims

In Claim 1, Column 17, Lines 66-67, delete "cathode-to cathode" and insert --cathode-to-cathode--, therefor.

In Claim 11, Column 18, Line 59-60, delete "cathode-to cathode" and insert --cathode-to-cathode--, therefor.

In Claim 26, Column 20, Lines 8-9, delete "cathode-to cathode" and insert --cathode-to-cathode--, therefor.

In Claim 27, Column 20, Line 18, delete "device s" and insert --device--, therefor.

In Claim 37, Column 20, Line 48, after "power" delete "to".

In Claim 37, Column 20, Line 59, after "that" delete "a".

In Claim 37, Column 21, Lines 7-8, delete "cathode-to cathode" and insert --cathode-to-cathode--, therefor.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*